United States Patent [19]

Lee et al.

[11] Patent Number: 5,681,851

[45] Date of Patent: Oct. 28, 1997

[54] EMULSIFIED COMPOSITIONS OF 1,4-BIS (BROMOACETOXY)-2-BUTENE USEFUL AS A MICROBICIDE AND PRESERVATIVE

[75] Inventors: James Lee; Vanja M. King; Xiangdong Zhou, all of Memphis, Tenn.

[73] Assignee: Buckman Laboratories International, Inc., Memphis, Tenn.

[21] Appl. No.: 472,209

[22] Filed: Jun. 7, 1995

[51] Int. Cl.$^6$ ................................................. A01N 37/06
[52] U.S. Cl. ................................................................ 514/547
[58] Field of Search ................................................ 514/547

[56] References Cited

U.S. PATENT DOCUMENTS

| | | | |
|---|---|---|---|
| 2,840,598 | 6/1958 | Schwartz | 260/187 |
| 2,873,249 | 2/1959 | Schwartz | 514/547 |
| 3,865,724 | 2/1975 | Shema et al. | 210/62 |
| 3,915,685 | 10/1975 | Koyna et al. | 71/67 |
| 4,022,605 | 5/1977 | Konya et al. | 71/67 |
| 4,066,786 | 1/1978 | Bent et al. | 514/547 |
| 5,026,723 | 6/1991 | Katayama et al. | 514/547 |
| 5,035,956 | 7/1991 | Sedun | 514/547 |

FOREIGN PATENT DOCUMENTS

| | | | |
|---|---|---|---|
| 2052989 | 2/1981 | United Kingdom | 514/547 |

OTHER PUBLICATIONS

Derwent Abstract AN 86–321451, Japanese Patent Application No. 61–236703, Oct. 22, 1986.
Chemical Abstract No. 91:163056r, "Bactericidal and Fungicidal Compositions," Chemical Abstracts vol. 91, 1979.
Material Safety Data Sheet, Product: Monolan 6400, dated Jul. 22, 1992.
Material Safety Data Sheet, Product: Toximul 8320, dated Jul. 24, 1990.
Material Safety Data Sheet, Product: Monafax 785, dated Jan. 16, 1992.
Material Safety Data Sheet, Product: T Mulz 734–2, dated Mar. 21, 1990.
Material Safety Data Sheet, Product: T Det XH, dated Aug. 18, 1994.
Material Safety Data Sheet, Product: T Mulz 598, dated Feb. 8, 1995.
Material Safety Data Sheet, Product: Emphos PS–236, dated Feb. 9, 1990.
Material Safety Data Sheet, Product: T Mulz 565, dated Dec. 14, 1989.
ASTM Standards on Materials and Environmental Microbiology, 1987, Standard Test Measure for Efficacy of Antimicrobials as Preservatives for Aqueous–Based Products Used in the Paper Industry (Bacterial Spoilage) pp. 278–283.
Mc Cutcheon's, vol. 1, Emulsifiers and Detergents, North American Ed. (1990) pp. 131, 190 & 191.
Mc Cutcheon's, Detergents and Emulsifiers 1971 Annual p. 183.
Mc Cutcheon's Detergents and Emulsifiers (1978) Annual, International Ed., pp. 115 & 195.

*Primary Examiner*—Allen J. Robinson
*Attorney, Agent, or Firm*—Armstrong, Westerman, Hattori, McLeland & Naughton

[57] ABSTRACT

An emulsifier composition containing 1,4-bis (bromoacetoxy)-2-butene (BBAB) is disclosed which has the ability to disperse and/or dissolve uniformly in aqueous systems thereby effectively controlling the growth of microorganisms. The composition contains BBAB and a nonionic emulsifier.

A method for inhibiting the growth of microorganisms with this composition in an amount effective to control the growth of microorganisms is also disclosed.

36 Claims, No Drawings

EMULSIFIED COMPOSITIONS OF 1,4-BIS (BROMOACETOXY)-2-BUTENE USEFUL AS A MICROBICIDE AND PRESERVATIVE

FIELD OF THE INVENTION

The present invention relates to emulsified compositions of 1,4-bis(bromoacetoxy)-2-butene and methods of using these emulsified compositions for microbicidal and preservative purposes.

BACKGROUND OF THE INVENTION

A large number of commercial, industrial, agricultural, and wood products are subject to microbiological attack which reduces or destroys their economic value. Examples of materials that may be subject to microbiological degradations are surface coatings, wood, agricultural seed, leather, and plastics, including flexible plastics. The temperature at which these products are stored and their intrinsic characteristics makes these products susceptible to the growth of microorganisms. These microorganisms can be introduced during the manufacturing of these products by exposure to air, tanks, pipes, equipment, and humans and/or during their use from multiple openings and reclosures of packaged products and by the introduction of contaminated objects to stir or remove material.

Aqueous systems containing organic materials are also highly subject to microbiological attack. Such aqueous systems include latexes, surfactants, dispersants, stabilizers, thickeners, adhesives, starches, waxes, proteins, emulsifying agents, detergents, cellulose products, and resins fromulated in aqueous solutions, emulsions or suspensions. These systems frequently contain relatively large amounts of water causing them to be well-suited environments for microbiological growth and thus attack and degradation. Microbiological degradation of aqueous systems containing organic materials may manifest itself as a variety of problems, such as loss of viscosity, gas formation, objectionable odors, decreased pH, emulsion breaking, color change, and gelling.

Another objectionable phenomenon occurring in industrial process systems involving water is slime formation. Slime consists of matted deposits of microorganisms, fibers and debris. It may be stringy, pasty, rubbery, tapioca-like, or hard, and may have a characteristic undesirable odor that is different or heightened from that of the liquid suspensions in which it is formed. The microorganisms involved in its formation are primarily different species of spore-forming and nonspore-forming bacteria, particularly encapsulated forms of bacteria which secrete gelatinous substances that envelop or encase the cells. Slime microorganisms also include filamentous bacteria, filamentous fungi of the mold type, yeasts, and yeast-like organisms. Slime reduces yields in paper production and causes plugging and other problems in water systems.

The solubility of 1,4-bis(bromoacetoxy)-2-butene ("BBAB") is very low in water. As a result, this compound will have great difficulty being dispersed in water. Because great limitation on the practicality of BBAB. If a compound cannot be dispersed or dissolved in water, then no matter how good its microbicide activity, it generally will not be used in commercial applications especially in view of the many aqueous systems that need to be treated with microbicides as described above. Accordingly, there is a need to develop a formulation or emulsion which permits the use of BBAB in aqueous systems. In other words, there is a need for an aqueous dispersable formulation containing BBAB.

SUMMARY OF THE INVENTION

An object of this invention is to provide a microbicidal formulation that is water dispersible and/or dissolvable that contains 1,4-bis(bromoacetoxy)-2-butene.

An additional object is to provide methods of making this formulation.

It is also an object of this invention to provide a method for controlling the growth of microorganisms in aqueous systems employing the above formulation as a microbicide.

Another object is to provide a method for controlling the formation of slime in an aqueous medium such as industrial cooling water or pulp and paper systems.

A further object of the present invention is to provide a method for controlling the growth of microorganisms on a substance suseptible to deterioration or disfigurement by microorganisms.

Additional features and advantages of the present invention will be set forth in part in the description which follows, and in part will be apparent from the description, or may be learned by practice of the present invention. The objectives and other advantages of the present invention will be realized and attained by means of the elements and combinations particularly pointed out in the written description and appended claims.

To achieve these and other advantages and in accordance with the purpose of the present invention, as embodied and broadly described herein, the present invention relates to an emulsified composition formulation containing 1,4-bis (bromoacetoxy)-2-butene and a non-ionic emulsifier having a molecular weight from about 500 to about 8,000 and an HLB value from about 7 to about 20.

An additional feature of the present invention relates to a method for controlling the growth of a microorganism in an aqueous system. This method includes the step of contacting an aqueous system susceptible to the growth of a microorganism with the emulsified composition in an amount effective to control the growth of the microorganism.

Another feature of the present invention is a method of controlling the formation of slime which includes the step of contacting an aqueous system susceptible to the formation of slime with the emulsified composition in an amount effective to control the formation of the slime.

A further feature of the present invention is a method of controlling microbiological deterioration or disfigurement. This method includes the step of contacting a substance susceptible to microbiological deterioration of disfigurement with the emulsified composition in an amount effective to control the growth of a microorganism.

It is to be understood that both the foregoing general description and the following detailed description are exemplary and explanatory only and are intended to provide further explanation of the present invention, as claimed.

DETAILED DESCRIPTION 1,4-bis(bromoacetoxy)-2-butene (BBAB) employed in the present invention has the following formula:

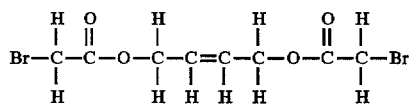

The synthesis of these compounds are described in U.S. Pat. No. 2,840,598, incorporated in its entirety by reference herein. The CAS No. for BBAB is 20679-58-7. BBAB has a molecular weight of 330 and is commercially available as a technical grade product from Bromine Compounds Ltd. In HPLC analysis, the technical grade of BBAB is about 87% BBAB, 4% 1-bromoacetoxy-4-dibromoacetoxy-2-butene (MBAB), and 4% of 1-bromoacetoxy-4-hydroxy-2-butene (BAHB). All of these compounds are active ingredients and are considered microbicides. For purposes of the present invention, BBAB can include the presence of one or more of these other compounds in small quantities.

The boiling point of BBAB is about 135°–136° C. at 0.005 mm Hg, and the freezing point of BBAB is below –20° C. The solubility of BBAB in water is extremely low. BBAB is soluble in dimethylformamide and ethylene glycol monomethylether. BBAB is also soluble in an isopropenol, n-butenol, glycerol, ethylene glycol, propylene glycol, and diethylene glycol. The specific gravity of the technical grade of BBAB is 1.74 at 20° C.

Because BBAB has a high specific gravity, it has a higher density than water which adds to the problem that BBAB does not disperse well into aqueous systems such as water. In other words, BBAB can be considered water insoluble.

The emulsified concentrated formulation of the present invention contains at least BBAB as an active ingredient. The formulation also contains a nonionic emulsifier that has a molecular weight range of from about 500 to about 8,000, preferably from about 800 to about 7,000 and more preferably from about 1,000 to about 6,000; and an HLB value of from about 7 to about 24, preferably from about 10 to about 20, and more preferably from about 13 to about 18.

Preferably, the formulation also contains an epoxidized oil, a hydrophilic solvent, and an anionic emulsifier.

The BBAB is generally present in the formulation of the present invention in an amount sufficient to control or inhibit the growth of at least one microorganism. Preferably, the amount of BBAB present is from about 80 wt % to about 90 wt %, and more preferably 82 wt % to about 87 wt %, and most preferably about 86 wt %. These weight percentages, as well as all other weight percentages referred to herein, are based on the total weight of the formulation.

The nonionic emulsifier is generally present in an amount from about 1 wt % to about 10 wt %, and preferably about 5 wt %. Generally, non-ionic emulsifiers or surfactants prepared by reacting $C_1$–$C_8$ alcohols, preferably $C_1$–$C_4$ alcohols, with ethylene oxide and propylene oxide can be used. In lieu of the propylene oxide as one of the reactants, butylene oxide could be used or a mixture of propylene oxide with butylene oxide. Alternatively, nonyl phenol reacted with ethylene oxide and optionally with propylene oxide, butylene oxide, or mixtures thereof can also be a suitable non-ionic emulsifier for purposes of the present invention. One preferred nonionic emulsifier is butoxy-polypropyleneoxypolyethyleneoxyethanol which has a molecular weight of 2990 or 3117 depending on the method of calculation, according to the manufacturing data. This compound is commercially available from Union Carbide (Danbury, Conn.) under the trade name Tergitol XD. Other commercial products which could also be used as the nonionic emulsifier are Toximul 8320 (a non-ionic alkoxylate), or 8322 from Stepan Co. (Northfield, Ill.), T Der XD and XH (an alkoxylated butyl alcohol) from Harcros Chemicals Inc. (Kansas City, Kans.), and Monolan 6400 (an ethylene oxide, propylene oxide-copolymer) from Henkel Corporation (Cinn., Ohio).

The anionic emulsifier preferably is a phosphate ester anionic emulsifier. This emulsifier is used in sufficient amounts to improve the stability of BBAB in solution. Preferably, the anionic emulsifier is present in an amount ranging from about 0.5 wt % to about 5 wt %, and more preferably about 1.5 wt %. One preferred anionic emulsifier with a phosphate ester functional group is Monofax 785 (an alkoxyphosphate) which has an HLB value of about 10 to about 12 and is available from Mona Industries, Inc. (Patterson, N.J.). Other commercially available and acceptable phosphate ester anionic emulsifiers are T-MULZ 565, 598, 734, or 800 (an organo phosphonic acid ester) from Harcros Chemicals Inc. (Kansas City, Kans.), Maphos from Mazer Chemicals (Gurnee, Iowa), and Antara or Gafac both from Rhone-Poulenc (Cranberry, N.J.). Another phosphate ester anionic emulsifier is Emphos PS-236 available from Witco Chemicals Corporation (New York, N.Y.).

The epoxidized oil should be compatible and inert to BBAB. It is also preferred that the epoxidized oil have a high density (i.e., greater than 1.0). Preferred epoxidized oils are epoxidized linseed oil and epoxidized soy bean oil. Generally, the epoxidized oil is present in an amount from about 1 wt % to about 10 wt %, and preferably about 5 wt %.

The hydrophilic solvent preferably has strong coupling ability and is preferably dipropylene glycol methylether. The amount of the hydrophilic solvent is preferably from about 1.0 wt % to about 5.0 wt %, and more preferably about 1.5 wt %. One function of the hydrophilic solvent is to reduce the chance of crystallization of BBAB at room or lower temperatures during storage.

The last preferred component in the formulation of the present invention is an antioxidation agent such as butylated hydroxyanisole ("BHA") or butylated hydroxytoluene ("BHT"). Other acceptable antioxidation agents are Tocopherol, propyl gallate, t-butyl hydroquinone, and di-t-butylhydroquinone. All of these antioxidation agents have the ability to also improve the stability of the overall formulation. Preferred amounts of the antioxidation agent are from about 0.1 wt % to about 5.0 wt %, and more preferably about 1.0 wt %.

One preferred formulation of the present invention is as follows:

| Formula A: | |
| --- | --- |
| Technical grade BBAB (includes 4% MBAB and 4% BHAB) | 86.0 wt % |
| Epoxidized linseed oil | 5.0 wt % |
| Tergitol XD | 5.0 wt % |
| Monafax 785 | 1.5 wt % |
| Dipropylene glycol methylether | 1.5 wt % |
| Butylated hydroxyanisole | 1.0 wt % |

It has been discovered that when lower amounts of the active ingredient are present such as amounts ranging from about 25.0 wt % to about 50.0 wt % of BBAB, the amount of the components that are preferred changes. In particular, with this range of BBAB, it is preferred to have the nonionic emulsifier, preferably Tergitol XD, present in an amount from about 5 wt % to about 15 wt %, and more preferably about 10 wt %. The anionic emulsifier, preferably Monofax 785, is preferably present in an amount from about 1.0 wt % to about 5 wt %, and more preferably about 3.0 wt %. Instead of a hydrophilic solvent, a hydrophobic solvent is used, preferably DMATO (dimethylamide of tall oil fatty acid), which is preferably present in an amount from about 10 wt % to about 45 wt %, and more preferably about 35 wt %. Other examples of hydrophobic solvents are aromatic solvents.

An epoxidized oil is preferably used, and most preferably an epoxidized oil with about 15 wt % mineral oil. The epoxidized oil is preferably present in an amount from about 5 wt % to about 10 wt %, and more preferably about 7.5 wt %. When no mineral oil is used, the epoxidized oil is preferably present in an amount from about 10 wt % to about 25 wt %, and more preferably about 16.5 wt %.

The antioxidation agent, which is preferably BHA or BHT, is present in the same amounts as described above.

Generally, in making the formulation of the present invention, the above described ingredients can simply be mixed together to form the formulation. The formulation of the present invention permits the use of the active ingredient, BBAB, in aqueous environments. In other words, the formulation of the present invention has the ability to disperse and/or dissolve in aqueous solutions, such as water. This is an important feature in controlling or inhibiting the growth of microorganisms which are present in aqueous systems. A formulation that does not disperse or dissolve in aqueous systems simply would not be proficient in controlling or inhibiting the growth of at least one microorganism and thus the formulation of the present invention has the ability to be effective in such aqueous systems due to its ability to disperse or dissolve in aqueous systems such as water.

The formulation of the present invention can also be further diluted by simply taking the formulation and diluting it with the appropriate amount of water to create the necessary wt % of the active ingredient for whatever need is called for. Again, a formulation that would not be so easily diluted would not be desirable in commercial applications where industry demands that a product be sold in concentrate form and then diluted at the site of use. The formulation of the present invention provides this advantage as well.

According to the methods of the present invention, controlling or inhibiting the growth of at least one microorganism includes both the reduction and/or the prevention of such growth.

It is to be further understood that by "controlling" (i.e., preventing) the growth of at least one of these types of microorganisms, the growth of at least microorganism is inhibited. In other words, there is no growth or essentially no growth of at least one microorganism. "Controlling" the growth of at least one microorganism maintains the microorganism population at a desired level, reduces the population to a desired level (even to undetectable limits, e.g., zero population), and/or inhibiting the growth of the microorganism. Thus, the substrates or materials susceptible to attack by these types of microorganisms are preserved from this attack and the resulting spoilage and other detrimental effects caused by the microorganisms. Further, it is also to be understood that "controlling" the growth of at least one microorganism also includes biostatically reducing and/or maintaining a low level of microorganisms such that the attack by microorganisms and any resulting spoilage or other detrimental effects are mitigated, i.e., the microorganism growth rate or microorganism attack rate is slowed down or eliminated.

As reflected in the examples set forth below, the formulation of the present invention containing 1,4-bis (bromoacetoxy)-2-butene is an effective preservative against bacteria and fungi in commonly used paper additives and coating materials, such as, but not limited to, clay, starch, calcium carbonate, titanium dioxide, carboxymethyl cellulose, hydroxyethyl cellulose, acrylic latex, cationic acrylamide polymers, anionic polyacrylamide polymers, alum, styrene-butadiene resins, and various other polymers.

Based on the ability of the formulation containing 1,4-bis (bromoacetoxy)-2-butene being effective against microorganisms in these paper additives and coating materials, it is clear that this composition is an effective preservative for an entire host of substrates and commercial, industrial, agricultural, and wood products.

Accordingly, the formulation containing 1,4-bis (bromoacetoxy)-2-butene can be used in a method for controlling the growth of at least one microorganism in an aqueous system which comprises contacting the system susceptible to the growth of the microorganism with the formulation containing 1,4-bis(bromoacetoxy)-2-butene in an amount effective to control the growth of the microorganism. The formulation containing 1,4-bis(bromoacetoxy) -2-butene may be added directly to the system under working conditions. Representative aqueous systems include aqueous solutions, emulsions, and suspensions. Specific systems include water-based paints and metalworking fluids.

The present invention also relates to a microbicidal composition comprising a formulation containing 1,4-bis (bromoacetoxy)-2-butene in an amount effective to control the growth of at least one microorganism and a non-pharmaceutically acceptable carrier. Non-pharmaceutically acceptable carriers include solvents, surfactants, and other carriers used in industrial applications as would be known to those skilled in the art. These non-pharmaceutically acceptable carriers do not have the low toxicity profiles and purity required of pharmaceutically acceptable carriers. Non-pharmaceutical grade water is specifically included in these non-pharmaceutical carriers.

The formulation containing 1,4-bis(bromoacetoxy)-2-butene can also be used in a method for controlling the formation of slime in an aqueous system susceptible to slime formation which comprises the step of contacting the aqueous system with the formulation containing 1,4-bis (bromoacetoxy)-2-butene in an amount effective to prevent the formation of slime. The formulation containing 1,4-bis (bromoacetoxy)-2-butene may be added directly to the system under working conditions. The formulation containing 1,4-bis(bromoacetoxy)-2-butene can be used to kill slime forming organisms, both bacteria and fungi. This method is effective in aqueous liquids such as a pulp slurry for use in papermaking or liquids contained in a water cooling device.

A further use of the formulation of the present invention resides in a method of controlling microbiological deterioration or disfigurement comprising the step of contacting a substance susceptible to microbiological deterioration or disfigurement with the formulation containing 1,4-bis (bromoacetoxy)-2-butene in an amount effective to inhibit the growth of the microorganism.

Microorganisms, as used herein, include, but are not limited to, bacteria and fungi, including both yeasts and molds. Examples of bacteria include *Pseudomonas aeruginosa* and *Ochrobactrum anthropi*. Example of fungi include *Aspergillus niger* (ATCC 9642).

The formulation containing 1,4-bis(bromoacetoxy)-2-butene may be applied to the substance or admixed with the components which make up the substance. This method is effective on substances such as wood, paint-film, leather, flexible plastic, textiles, and the like. In the preservation of leather, these compounds can be absorbed onto the hides and thus can be used in the long term preservation of leather. Similarly, in wood preservation applications, the formulation containing the 1,4-bis(bromoacetoxy)-2-butene provides a method for inhibiting the growth of wood-decaying organisms over a short or long period of time.

The formulations of the present invention have a number of advantages over other known microbicides. They are excellent microbicides to be used for both preservation of paint while in the can and after application on the painted surface. They are hydrolytically stable over a wide pH range (3–9) and can be used in both latex and oil-based systems. They are soluble in many solvents, and may therefore be readily diluted for convenience of use. Their compatibility and efficiency makes them advantageous for use as a microbicide in plastic, and for impregnation in or application on the surface of wood, paper, cloth or other materials.

The effective amount or percentage of active compounds necessary to achieve the desired result will vary somewhat depending on the substrate or aqueous system to be protected, the conditions for microbial growth, and the degree of protection desired. The concentration of the compounds of the present invention generally ranges from about 0.0001% to 4% (w/w); preferably 0.0001% to 0.2%, and more preferably 0.0005% to 0.0050% in the composition applied. One of ordinary skill can readily determine the effective amount required for a particular application by simply testing various concentrations prior to treatment of the entire effected substrate or system.

With aqueous systems, a preferred effective amount of active compound ranges from about 20 to 5000 parts per million, and more preferably, from about 250 to 2000 parts per million of the aqueous system. The amount of bis 1,4-(bromoacetoxy)-2-butene effective to prevent the formation of slime in an aqueous liquid preferably ranges from about 1 to about 200 parts per million, and more preferably, from about 1 to 25 parts per million of the aqueous liquid.

The following examples are given to illustrate the nature of the invention. It should be understood, however, that the invention is not to be limited to the specific conditions or details set forth in these examples.

The present invention will be further clarified by the following examples, which are intended to be purely exemplary of the invention.

EXAMPLE 1

Preparation of formulation containing 1,4-bis (bromoacetoxy)-2-butene

The formulation of formula A described above, was prepared by adding all of the ingredients into a reactor at room temperature with constant stirring until the solution became homogeneous insuring that BHA had completely dissolved in the solution.

EXAMPLE 2

Materials and Methods

1. Biocide
FORMULA A
2. Materials Preserved
   (1) 30% aqueous solution of clay, pH=3.2
   (2) 30% aqueous solution of uncooked starch, pH=5.8.
   (3) 30% aqueous solution of calcium carbonate, pH=9.0.
   (4) 30% aqueous solution of titanium dioxide, pH=7.0.
   (5) 5% aqueous solution of carboxymethyl cellulose (CMC), pH=6.5.
   (6) 5% aqueous solution of hydroxyethyl cellulose (HEC), pH=6.0.
   (7) 50% aqueous solution of acrylic latex (the original latex contains 51% solid) used as paint ingredient, pH=5.5.
   (8) 1% aqueous solution of BFL 950 (a cationic acrylamide polymer), pH=4.1.
   (9) 1% aqueous solution of BL 606 (an anionic polyacrylamide polymer), pH=6.2.
   (10) 5% aqueous solution of alum (48% aluminum sulfate), pH=3.5.
   (11) 30% aqueous solution of styrene-butadiene resin (SBR), pH=7.0.
3. Microorganisms The bacterial inoculum was a mixture of *Pseudomonas aeruginosa* and *Ochrobactrum anthropi* which were previously isolated from a naturally contaminated paint. The fungal inoculum was a laboratory strain of *Aspergillus niger* (ATCC 9642).

Both bacteria and fungi were acclimated in the above aqueous solutions for at least two weeks until adequate growth was presented in the solution. The spoiled materials were then used as the inocula for the challenge tests.

4. Culture Medium

Difco dehydrated tryprone glucose extract (TGE) agar was used for plating in antibacterial test. Difco dehydrated Sabouraud's agar was used for plating in antifungal test.

5. Procedure
   (1) Bacterial Challenge Test.

To each 4-oz glass bottle was added 50 ml of aqueous solution of the above materials to be preserved, followed by the addition of a desired volume of the formulation of formula A ("Busan 1210®") to give a desired biocide concentration in parts per million (ppm). The biocide concentrations for clay, $CaCO_3$, $TiO_2$, and uncooked starch were 100, 500, 1000, and 2000 ppm, and for CMC, HEC, SBR, alum, BFL 590, and BL 606 were 200, 500, and 1000 pm, and for acrylic latex were 200, 500, 1000, 2000 ppm. Controls without addition of biocide were included for each material to be preserved. The pH of each above aqueous solution was measured before the biocide addition. The samples (treated and control) were inoculated by adding about 2 ml of the specific spoiled material to give a bacterial count of approximately $10^6$/ml. Immediately after the inoculation, the controls were plated to determine the actual inoculum concentration. All the samples including controls and treatments were incubated at room temperature with the bottles loosely capped. At the end of each week's incubation, one ml of liquid was withdrawn from each sample (control and treatment) and plated on TGE agar to determine the number of survivors. All plates were incubated at room temperature for 5 days before counting. The tests were conducted for six weeks with weekly sampling. Immediately after each week's sampling, the treated samples were rechallenged with 2 ml of bacterial inoculum from one of the duplicated controls.

All the treatments and controls were duplicated in the test. After each addition (including biocide, inoculum and the rechallenge), the bottles were vigorously shaken to mix the samples thoroughly. A biocide concentration that can provide a 95% or more reduction in count was considered as the effective concentration to preserve the material.

(2) Fungal Challenge Test.

The procedure for the antifungal test is very similar to that used for the antibacterial test described above. The differences from the above procedure were as follows.

The inocula were the spoiled materials containing *A. niger* which was previously acclimated in the material solutions for several weeks. The inoculum size for each sample was about $10^5$ spores/ml. Sabouraud's agar instead of TGE agar was used as the recovery medium for the fungal growth. Streak cultures (instead of dilution plating) were prepared on Sabouraud's agar weekly for all inoculated samples (controls and treatments) to determine the levels of fungi present. Fungal growth was judged on a growth-no-growth basis. A biocide concentration that can provide no fungal growth on the plates was considered as the effective concentration to preserve the material.

The procedures, as set forth in the manual of "ASTM Standards on Materials and Environmental Microbiology" (1st ed. 1987, pp. 278–282), were followed.

TABLE 1

Efficacy of Busan 1210 Against Bacteria in 30% Slurry of Clay

| BS1210 (ppm) | Week 1 (cfu/ml)* | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $1.2 \times 10^7$ | $1.4 \times 10^7$ | $1.1 \times 10^7$ | $5.4 \times 10^7$ | $2.6 \times 10^7$ | $4.1 \times 10^7$ |
| 0 (control) | $1.4 \times 10^7$ | $1.9 \times 10^7$ | $1.2 \times 10^7$ | $3.1 \times 10^7$ | $4.4 \times 10^7$ | $7.3 \times 10^7$ |
| 100 | $6.8 \times 10^6$ | $2.3 \times 10^7$ | Not Tested | Not Tested | Not Tested | Not Tested |
| 100 | $9.6 \times 10^4$ | $3.5 \times 10^7$ | Not Tested | Not Tested | Not Tested | Not Tested |
| 500 | <10# | <10 | <10 | <10 | <10 | <10 |
| 500 | <10 | <10 | <10 | <10 | <10 | <10 |
| 1000 | <10 | <10 | <10 | <10 | <10 | <10 |
| 1000 | <10 | <10 | <10 | <10 | <10 | <10 |
| 2000 | <10 | <10 | <10 | <10 | <10 | <10 |
| 2000 | <10 | <10 | <10 | <10 | <10 | <10 |

TABLE 2

Efficacy of Busan 1210 Against Bacteria in 30% Slurry of TiO$_2$

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $3.3 \times 10^7$ | $3.1 \times 10^7$ | $4.0 \times 10^7$ | $8.4 \times 10^7$ | $1.6 \times 10^8$ | $1.9 \times 10^8$ |
| 0 (control) | $3.1 \times 10^7$ | $2.8 \times 10^7$ | $2.2 \times 10^7$ | $9.2 \times 10^7$ | $2.1 \times 10^8$ | $1.8 \times 10^8$ |
| 100 | $6.4 \times 10^6$ | $2.4 \times 10^7$ | Not Tested | Not Tested | Not Tested | Not Tested |
| 100 | $3.2 \times 10^6$ | $1.8 \times 10^7$ | Not Tested | Not Tested | Not Tested | Not Tested |
| 500 | $6.0 \times 10^1$ | $2.5 \times 10^2$ | $2.6 \times 10^2$ | $4.6 \times 10^3$ | $1.1 \times 10^5$ | $7.8 \times 10^6$ |
| 500 | $1.5 \times 10^3$ | $1.4 \times 10^2$ | $5.8 \times 10^3$ | $7.8 \times 10^5$ | $1.8 \times 10^6$ | $1.1 \times 10^7$ |
| 1000 | <10 | <10 | <10 | <10 | <10 | $4.3 \times 10^3$ |
| 1000 | <10 | <10 | <10 | <10 | <10 | $8.0 \times 10^2$ |
| 2000 | <10 | <10 | <10 | <10 | <10 | <10 |
| 2000 | <10 | <10 | <10 | <10 | <10 | <10 |

*cfu - colony forming unit.
<10# represents a cfu/ml between 0 and 9 because the dilution limitations is $10^1$ for plate counting.

TABLE 3

Efficacy of Busan 1210 Against Bacteria in 30% Slurry of CaCO$_3$

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $6.3 \times 10^7$ | $4.6 \times 10^7$ | $3.8 \times 10^7$ | Not Tested | Not Tested | Not Tested |
| 0 (control) | $6.8 \times 10^7$ | $6.2 \times 10^7$ | $6.2 \times 10^7$ | Not Tested | Not Tested | Not Tested |
| 100 | $5.4 \times 10^7$ | $5.3 \times 10^7$ | Not Tested | Not Tested | Not Tested | Not Tested |
| 100 | $3.1 \times 10^7$ | $4.8 \times 10^7$ | Not Tested | Not Tested | Not Tested | Not Tested |
| 500 | $6.1 \times 10^5$ | $1.4 \times 10^7$ | $2.1 \times 10^7$ | Not Tested | Not Tested | Not Tested |
| 500 | $4.1 \times 10^5$ | $1.1 \times 10^7$ | $2.3 \times 10^7$ | Not Tested | Not Tested | Not Tested |
| 1000 | $7.2 \times 10^4$ | $1.1 \times 10^7$ | $1.8 \times 10^7$ | Not Tested | Not Tested | Not Tested |
| 1000 | $8.5 \times 10^4$ | $8.9 \times 10^6$ | $2.2 \times 10^7$ | Not Tested | Not Tested | Not Tested |
| 2000 | $7.7 \times 10^3$ | $2.3 \times 10^5$ | $8.4 \times 10^6$ | Not Tested | Not Tested | Not Tested |
| 2000 | $8.2 \times 10^3$ | $3.6 \times 10^5$ | $1.2 \times 10^7$ | Not Tested | Not Tested | Not Tested |

TABLE 4

Efficacy of Busan 1210 Against Bacteria in 30% Slurry of Uncooked Starch

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $2.8 \times 10^7$ | $2.1 \times 10^7$ | $4.6 \times 10^7$ | $5.5 \times 10^7$ | $8.9 \times 10^7$ | $9.6 \times 10^7$ |
| 0 (control) | $2.5 \times 10^7$ | $1.8 \times 10^7$ | $8.9 \times 10^7$ | $6.3 \times 10^7$ | $7.4 \times 10^7$ | $8.3 \times 10^7$ |
| 100 | $4.8 \times 10^6$ | $1.4 \times 10^7$ | Not Tested | Not Tested | Not Tested | Not Tested |
| 100 | $1.4 \times 10^6$ | $1.2 \times 10^7$ | Not Tested | Not Tested | Not Tested | Not Tested |
| 500 | $1.0 \times 10^5$ | <10 | <10 | <10 | <10 | <10 |
| 500 | $1.4 \times 10^3$ | <10 | <10 | <10 | <10 | <10 |
| 1000 | <10 | <10 | <10 | <10 | <10 | <10 |
| 1000 | <10 | <10 | <10 | <10 | <10 | <10 |
| 2000 | <10 | <10 | <10 | <10 | <10 | <10 |
| 2000 | $1.3 \times 10^2$ | <10 | <10 | <10 | <10 | <10 |

TABLE 5

Efficacy of Busan 1210 Against Bacteria in 5% Solution of CMC

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $6.2 \times 10^6$ | $8.3 \times 10^6$ | $1.1 \times 10^7$ | $1.6 \times 10^7$ | $1.1 \times 10^7$ | $1.0 \times 10^7$ |
| 0 (control) | $6.5 \times 10^6$ | $8.7 \times 10^6$ | $1.0 \times 10^7$ | $1.2 \times 10^7$ | $1.2 \times 10^7$ | $1.2 \times 10^7$ |
| 200 | $3.4 \times 10^3$ | $7.7 \times 10^3$ | $3.4 \times 10^6$ | $6.8 \times 10^6$ | Not Tested | Not Tested |
| 200 | $4.2 \times 10^3$ | $9.6 \times 10^3$ | $2.8 \times 10^6$ | $4.5 \times 10^6$ | Not Tested | Not Tested |
| 500 | <10 | <10 | $9.4 \times 10^2$ | $1.2 \times 10^3$ | $9.0 \times 10^2$ | $4.3 \times 10^3$ |
| 500 | <10 | <10 | $2.3 \times 10^2$ | $6.8 \times 10^2$ | $1.5 \times 10^3$ | $4.1 \times 10^3$ |
| 1000 | <10 | <10 | <10 | <10 | <10 | <10 |
| 1000 | <10 | <10 | <10 | <10 | <10 | <10 |

TABLE 6

Efficacy of Busan 1210 Against Bacteria in 5% Solution of HEC

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $1.8 \times 10^7$ | $2.3 \times 10^7$ | $1.2 \times 10^7$ | $2.1 \times 10^7$ | $1.1 \times 10^7$ | $1.7 \times 10^7$ |
| 0 (control) | $1.7 \times 10^7$ | $2.2 \times 10^7$ | $1.4 \times 10^7$ | $2.7 \times 10^7$ | $1.2 \times 10^7$ | $1.5 \times 10^7$ |
| 200 | $9.0 \times 10^2$ | $7.6 \times 10^3$ | $1.1 \times 10^6$ | Not Tested | Not Tested | Not Tested |
| 200 | $2.2 \times 10^3$ | $1.2 \times 10^4$ | $1.1 \times 10^6$ | Not Tested | Not Tested | Not Tested |
| 500 | $2.8 \times 10^3$ | $3.1 \times 10^3$ | $8.1 \times 10^2$ | $1.4 \times 10^3$ | $5.6 \times 10^3$ | $7.4 \times 10^3$ |
| 500 | $1.8 \times 10^3$ | $5.6 \times 10^3$ | $1.5 \times 10^3$ | $2.7 \times 10^3$ | $1.4 \times 10^3$ | $8.6 \times 10^3$ |
| 1000 | $2.8 \times 10^3$ | $1.2 \times 10^2$ | $1.0 \times 10^2$ | $1.4 \times 10^2$ | $2.0 \times 10^2$ | $3.1 \times 10^2$ |
| 1000 | $7.0 \times 10^2$ | $1.1 \times 10^2$ | $6.0 \times 10^2$ | $6.2 \times 10^2$ | $2.0 \times 10^2$ | $4.6 \times 10^2$ |

TABLE 7

Efficacy of Busan 1210 Against Bacteria in 50% Solution of Acrylic Latex

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $7.4 \times 10^5$ | $2.1 \times 10^6$ | $1.4 \times 10^6$ | $2.3 \times 10^6$ | $6.8 \times 10^6$ | $3.2 \times 10^8$ |
| 0 (control) | $8.3 \times 10^5$ | $3.3 \times 10^6$ | $1.2 \times 10^6$ | $2.7 \times 10^6$ | $7.8 \times 10^5$ | $4.2 \times 10^6$ |
| 200 | <10 | $4.6 \times 10^2$ | $1.9 \times 10^4$ | $3.6 \times 10^5$ | $2.3 \times 10^5$ | $3.0 \times 10^7$ |
| 200 | <10 | $1.4 \times 10^2$ | $2.2 \times 10^4$ | $7.2 \times 10^5$ | $4.1 \times 10^5$ | $1.6 \times 10^5$ |
| 500 | <10 | <10 | $4.6 \times 10^3$ | $3.1 \times 10^3$ | $2.0 \times 10^5$ | $2.3 \times 10^2$ |
| 500 | <10 | <10 | $5.2 \times 10^3$ | $6.8 \times 10^3$ | <10 | $1.0 \times 10^3$ |
| 1000 | <10 | <10 | <10 | <10 | <10 | $3.0 \times 10^2$ |
| 1000 | <10 | <10 | <10 | <10 | <10 | <10 |

TABLE 8

Efficacy of Busan 1210 Against Bacteria in 5% Solution of Alum

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $1.2 \times 10^6$ | $2.8 \times 10^6$ | $4.4 \times 10^6$ | $7.4 \times 10^6$ | $4.5 \times 10^6$ | $5.4 \times 10^6$ |
| 0 (control) | $7.4 \times 10^5$ | $1.1 \times 10^6$ | $4.8 \times 10^6$ | $8.7 \times 10^6$ | $5.6 \times 10^6$ | $4.1 \times 10^6$ |
| 200 | <10 | <10 | $2.1 \times 10^5$ | $1.3 \times 10^6$ | Not Tested | Not Tested |
| 200 | <10 | <10 | $8.6 \times 10^4$ | $7.7 \times 10^3$ | Not Tested | Not Tested |
| 500 | <10 | <10 | <10 | $3.3 \times 10^2$ | $1.3 \times 10^2$ | $4.0 \times 10^3$ |
| 500 | <10 | <10 | <10 | $2.4 \times 10^2$ | $5.1 \times 10^2$ | $2.0 \times 10^2$ |
| 1000 | <10 | <10 | <10 | <10 | <10 | <10 |
| 1000 | <10 | <10 | <10 | <10 | <10 | <10 |

TABLE 9

Efficacy of Busan 1210 Against Bacteria in 1% Solution of BFL 590

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $2.1 \times 10^4$ | $3.6 \times 10^5$ | $6.4 \times 10^7$ | $7.8 \times 10^7$ | $4.2 \times 10^7$ | $1.5 \times 10^8$ |
| 0 (control) | $4.8 \times 10^4$ | $5.8 \times 10^5$ | $7.5 \times 10^7$ | $8.9 \times 10^7$ | $4.5 \times 10^7$ | $1.2 \times 10^8$ |
| 200 | <10 | <10 | <10 | <10 | <10 | <10 |
| 200 | <10 | <10 | <10 | <10 | <10 | <10 |
| 500 | <10 | <10 | <10 | <10 | <10 | <10 |
| 500 | <10 | <10 | <10 | <10 | <10 | <10 |
| 1000 | <10 | <10 | <10 | <10 | <10 | <10 |
| 1000 | <10 | <10 | <10 | <10 | <10 | <10 |

TABLE 10

Efficacy of Busan 1210 Against Bacteria in 1% Solution of BL 606

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $8.2 \times 10^7$ | $8.9 \times 10^7$ | $8.2 \times 10^7$ | $8.8 \times 10^7$ | $6.8 \times 10^7$ | $6.4 \times 10^7$ |
| 0 (control) | $9.4 \times 10^7$ | $9.2 \times 10^7$ | $8.8 \times 10^7$ | $9.2 \times 10^7$ | $5.3 \times 10^7$ | $5.1 \times 10^7$ |
| 200 | $9.6 \times 10^4$ | $8.4 \times 10^4$ | $3.6 \times 10^6$ | $7.9 \times 10^4$ | Not Tested | Not Tested |
| 200 | $2.1 \times 10^2$ | $4.9 \times 10^2$ | $4.8 \times 10^6$ | $8.2 \times 10^6$ | Not Tested | Not Tested |
| 500 | <10 | <10 | <10 | <10 | <10 | $2.0 \times 10^3$ |
| 500 | <10 | <10 | <10 | <10 | $9.3 \times 10^2$ | $3.8 \times 10^3$ |
| 1000 | <10 | <10 | <10 | <10 | <10 | <10 |
| 1000 | <10 | <10 | <10 | <10 | <10 | <10 |

TABLE 11

Efficacy of Busan 1210 Against Bacteria in 30% Solution or SBR

| BS1210 (ppm) | Week 1 (cfu/ml) | Week 2 (cfu/ml) | Week 3 (cfu/ml) | Week 4 (cfu/ml) | Week 5 (cfu/ml) | Week 6 (cfu/ml) |
|---|---|---|---|---|---|---|
| 0 (control) | $8.7 \times 10^7$ | $8.4 \times 10^7$ | $1.3 \times 10^8$ | $1.1 \times 10^8$ | $1.7 \times 10^8$ | $1.1 \times 10^8$ |
| 0 (control) | $9.2 \times 10^7$ | $9.3 \times 10^7$ | $1.1 \times 10^8$ | $1.8 \times 10^8$ | $1.9 \times 10^8$ | $1.5 \times 10^8$ |
| 200 | $1.0 \times 10^2$ | $8.6 \times 10^2$ | $1.0 \times 10^2$ | $3.6 \times 10^3$ | $3.0 \times 10^2$ | $2.0 \times 10^3$ |
| 200 | $4.0 \times 10^2$ | $2.3 \times 10^3$ | $2.0 \times 10^2$ | $4.7 \times 10^3$ | $8.0 \times 10^2$ | $4.0 \times 10^2$ |
| 500 | <10 | <10 | <10 | <10 | <10 | <10 |
| 500 | <10 | <10 | <10 | <10 | <10 | <10 |
| 1000 | <10 | <10 | <10 | <10 | <10 | <10 |
| 1000 | <10 | <10 | <10 | <10 | <10 | <10 |

TABLE 12

Efficacy of Busan 1210 Against *A. niger* in 30% Slurry of Clay

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | − | − | − | + |
| 200 | − | − | − | − | − | + |
| 500 | − | − | − | − | − | − |
| 500 | − | − | − | − | − | − |
| 1000 | − | − | − | − | − | − |
| 1000 | − | − | − | − | − | − |

TABLE 13

Efficacy of Busan 1210 Against *A. niger* in 30% Slurry in TiO$_2$

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | + | Not Tested | Not Tested | Not Tested | Not Tested | Not Tested |
| 200 | + | Not Tested | Not Tested | Not Tested | Not Tested | Not Tested |
| 500 | − | + | Not Tested | Not Tested | Not Tested | Not Tested |
| 500 | − | + | Not Tested | Not Tested | Not Tested | Not Tested |
| 1000 | − | − | − | + | + | Not Tested |
| 1000 | − | − | − | + | + | Not Tested |
| 2000 | − | − | − | − | − | − |
| 2000 | − | − | − | − | − | − |

+growth observed;
−No growth.

TABLE 14

Efficacy of Busan 1210 Against *A. niger* in 30% Slurry in CaCO$_3$

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | Not Tested | Not Tested | Not Tested | Not Tested |
| 0 (control) | + | + | Not Tested | Not Tested | Not Tested | Not Tested |
| 500 | + | + | Not Tested | Not Tested | Not Tested | Not Tested |
| 500 | + | + | Not Tested | Not Tested | Not Tested | Not Tested |
| 1000 | + | + | Not Tested | Not Tested | Not Tested | Not Tested |
| 1000 | + | + | Not Tested | Not Tested | Not Tested | Not Tested |
| 2000 | − | + | Not Tested | Not Tested | Not Tested | Not Tested |
| 2000 | − | + | Not Tested | Not Tested | Not Tested | Not Tested |

TABLE 15

Efficacy of Busan 1210 Against *A. niger* in 30% Slurry in Uncooked Starch

| BS1210(ppm) | Week 1 (growth) | Week 2 (growth) | Week 3 (growth) | Week 4 (growth) | Week 5 (growth) | Week 6 (cfu/ml) |
|---|---|---|---|---|---|---|
| 0 (control) | + | + | + | + | + | + |
| 0 (control) | + | + | + | + | + | + |
| 200 | − | − | − | − | − | − |
| 200 | − | − | − | − | − | − |
| 500 | − | − | − | − | − | − |
| 500 | − | − | − | − | − | − |
| 1000 | − | − | − | − | − | − |
| 1000 | − | − | − | − | − | − |

TABLE 16

**Efficacy of Busan 1210 Against *A. niger* in 30% Slurry of CMC**

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | + | Not Tested | Not Tested | Not Tested |
| 200 | − | − | + | Not Tested | Not Tested | Not Tested |
| 500 | − | − | − | − | + | Not Tested |
| 500 | − | − | − | − | + | Not Tested |
| 1000 | − | − | − | − | − | − |
| 1000 | − | − | − | − | − | − |

TABLE 17

**Efficacy of Busan 1210 Against *A. niger* in 30% Slurry of HEC**

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | + | Not Tested | Not Tested | Not Tested |
| 200 | − | − | + | Not Tested | Not Tested | Not Tested |
| 500 | − | − | − | − | + | Not Tested |
| 500 | − | − | − | − | + | Not Tested |
| 1000 | − | − | − | − | − | − |
| 1000 | − | − | − | − | − | − |

TABLE 18

**Efficacy of Busan 1210 Against *A. niger* in 30% Slurry of Acrylic Latex**

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | + | Not Tested | Not Tested | Not Tested |
| 200 | − | − | + | Not Tested | Not Tested | Not Tested |
| 500 | − | − | + | Not Tested | Not Tested | Not Tested |
| 500 | − | − | + | Not Tested | Not Tested | Not Tested |
| 1000 | − | − | − | + | + | Not Tested |
| 1000 | − | − | − | + | + | Not Tested |
| 2000 | − | − | − | − | − | − |
| 2000 | − | − | − | − | − | − |

TABLE 19

**Efficacy of Busan 1210 Against *A. niger* in 30% Slurry of Alum**

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | − | + | Not Tested | Not Tested |
| 200 | − | − | − | + | Not Tested | Not Tested |
| 500 | − | − | − | − | − | − |
| 500 | − | − | − | − | − | − |
| 1000 | − | − | − | − | − | − |
| 1000 | − | − | − | − | − | − |

TABLE 20

**Efficacy of Busan 1210 Against *A. niger* in 1% Slurry of BFL 590**

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | − | + | Not Tested | Not Tested |
| 200 | − | − | − | + | Not Tested | Not Tested |
| 500 | − | − | − | − | − | − |
| 500 | − | − | − | − | − | − |
| 1000 | − | − | − | − | − | − |
| 1000 | − | − | − | − | − | − |

TABLE 21

**Efficacy of Busan 1210 Against *A. niger* in 1% Slurry of BL 606**

| BS1210(ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | + | Not Tested | Not Tested | Not Tested |
| 200 | − | − | + | Not Tested | Not Tested | Not Tested |
| 500 | − | − | − | + | + | Not Tested |
| 500 | − | − | − | + | + | Not Tested |
| 1000 | − | − | − | − | − | − |
| 1000 | − | − | − | − | − | − |

TABLE 22

**Efficacy of Busan 1210 Against *A. niger* in 30% Solution of SBR**

| BS1210 (ppm) | Week 1 (growth) | Week 2 (growth) | Week 3 (growth) | Week 4 (growth) | Week 5 (growth) | Week 6 (growth) |
|---|---|---|---|---|---|---|
| 0 (control) | + | + | + | + | + | + |
| 0 (control) | + | + | + | + | + | + |
| 200 | − | − | − | + | Not Tested | Not Tested |
| 200 | − | − | − | + | Not Tested | Not Tested |
| 500 | − | − | − | − | − | − |
| 500 | − | − | − | − | − | − |
| 1000 | − | − | − | − | − | − |
| 1000 | − | − | − | − | − | − |

TABLE 23

Summary of Effective Busan 1210 Concentrations vs Bacteria & Fungi for Six Weeks in All Materials

| Material Preserved | Effective Concentration vs Bacteria (ppm) | Effective Concentration vs *A. niger* (ppm) |
|---|---|---|
| Clay (30%) | 500, 1000, 2000 | 500, 1000 |
| TiO$_2$ (30%) | 1000, 2000 | 2000 |
| CaCO$_3$ (30%) | 2000 ppm for only 2-weeks | 2000 ppm only for 1-week |
| Uncooked Starch (30%) | 500, 1000, 2000 | 200, 500, 1000 |
| CMC (5%) | 500, 1000 | 1000 |
| HEC (5%) | 1000 | 1000 |
| Acrylic latex (50%) | 500, 1000 | 2000 |
| Alum (9%) | 500, 1000 | 500, 1000 |
| BFL 590 (1%) | 200, 500, 1000 | 500, 1000 |
| BL 606 (1%) | 500, 1000 | 1000 |
| SBR (30%) | 200, 500, 1000 | 500, 1000 |

*Table 23 summarizes the effective concentrations of Busan 1210 to preserve the above materials for the entire six weeks versus bacteria and fungi.

Table 23 sets forth the summary of the results showing bis 1,4-(bromoacetoxy)-2-butene to be an effective microbicide and preservative.

Other embodiments of the present invention will be apparent to those skilled in the art from consideration of the specification and practice of the invention disclosed herein. It is intended that the specification and examples be considered exemplary only, with a true scope and spirit of the invention being indicated by the following claims.

What is claimed:

1. A microbicidal formulation that is dispersible in an aqueous system comprising
   (a) about 80 wt % to about 90 wt % based on total weight of formulation of 1,4-bis(bromoacetoxy)-2-butene; and
   (b) about 1 wt % to about 10 wt % of a nonionic emulsifier having a molecular weight of from about 500 to about 8,000 and a HLB value of from about 7 to about 20.

2. The composition of claim 1, further comprising an epoxidized oil.

3. The composition of claim 2, wherein said epoxidized oil is epoxidized linseed oil or epoxidized soybean oil.

4. The composition of claim 1, further comprising an anionic emulsifier.

5. The composition of claim 4, wherein said anionic emulsifier has a phosphate ester functional group.

6. The composition of claim 1, further comprising an antioxidation agent.

7. The composition of claim 6, wherein said antioxidation agent is BHA or BHT.

8. The composition of claim 1, further comprising an epoxidized oil, a hydrophilic or hydrophobic solvent, an anionic emulsifier and an antioxidation agent.

9. A microbicidal formulation that is dispersible in an aqueous system comprising
   (a) 1,4-bis(bromoacetoxy)-2-butene;
   (b) about 1 wt % to about 10 wt % of a nonionic emulsifier having a molecular weight of from about 500 to about 8,000 and a HLB value of from about 7 to about 20; and
   (c) a hydrophilic solvent;
   wherein said 1,4-bis(bromoacetoxy)-2-butene is present in an amount at least about 50 wt % of said composition.

10. The composition of claim 9, wherein said hydrophilic solvent is dipropylene glycol methylether.

11. A microbicidal formulation that is dispersible in an aqueous system comprising
    (a) 1,4-bis(bromoacetoxy)-2-butene;
    (b) about 1 wt % to about 10 wt % of a nonionic emulsifier having a molecular weight of from about 500 to about 8,000 and a HLB value of from about 7 to about 20; and
    (c) a hydrophobic solvent;
    wherein said 1,4-bis(bromoacetoxy)-2-butene is present in an amount from about 25 wt % to about 50 wt % of said composition.

12. The composition of claim 11, further comprising mineral oil.

13. A method for controlling the growth of at least one microorganism in an aqueous system comprising the step of contacting an aqueous system susceptible to the growth of a microorganism with a composition comprising:
    (a) 1,4-bis(bromoacetoxy)-2-butene present in an amount of at least about 50 wt % of said solution; and
    (b) a nonionic emulsifier having a molecular weight of from about 500 to about 8,000 and a HLB value of from about 7 to about 20;
    wherein said composition is present in an amount effective to control the growth of said microorganism.

14. The method of claim 13, wherein the composition further comprises an epoxidized oil, a hydrophilic solvent, an anionic emulsifier and an antioxidation agent.

15. The method of claim 13, wherein said microorganism is a bacterium or a fungus.

16. The method of claim 13, wherein said aqueous system is an aqueous-based solution, an aqueous-based emulsion or an aqueous-based suspension.

17. The method of claim 16, wherein said aqueous-based emulsion is a paint.

18. The method of claim 16, wherein said aqueous-based solution is a metalworking fluid.

19. The method of claim 13, wherein said effective amount is from about 20 to about 5000 ppm of said aqueous system.

20. The method of claim 19, wherein said effective amount is from about 250 to about 2000 ppm of said aqueous system.

21. A method of controlling the formation of slime comprising the step of contacting an aqueous system susceptible to the formation of slime with a composition comprising:
    (a) 1,4-bis(bromoacetoxy)-2-butene; and
    (b) a nonionic emulsifier having a molecular weight of from about 500 to about 8,000 and a HLB value of from about 7 to about 20;
    wherein said composition is present in an amount effective to control the formation of said slime.

22. The method of claim 21, wherein the composition further comprises an epoxidized oil, a hydrophilic or hydrophobic solvent, an anionic emulsifier and an antioxidation agent.

23. The method of claim 21, wherein said effective amount is from about 1 to about 200 ppm of said aqueous system.

24. The method of claim 23, wherein said effective amount is from about 5 to about 25 ppm of said aqueous system.

25. The method of claim 21, wherein said aqueous system is a pulp slurry.

26. The method of claim 21, wherein said aqueous system is contained in a water cooling device.

27. A method of controlling microbiological deterioration or disfigurement comprising the step of contacting a substance susceptible to microbiological deterioration or disfigurement with a composition comprising:
    (a) 1,4-bis(bromoacetoxy)-2-butene; and
    (b) a nonionic emulsifier having a molecular weight of from about 500 to about 8,000 and a HLB value of from about 7 to about 20;
    wherein said composition is present in an amount effective to control the growth of at least one microorganism.

28. The method of claim 27, wherein the composition further comprises an epoxidized oil, a hydrophilic or hydrophobic solvent, an anionic emulsifier and an antioxidation agent.

29. The method of claim 27, wherein said contacting step is a step of applying said composition to said substance.

30. The method of claim 29, wherein said contacting step is a step of admixing said composition with the components which constitute the surface of said substance.

31. The method of claim 29, wherein said substance is wood.

32. The method of claim 29, wherein said substance is paint-film.

33. The method of claim 29, wherein said substance is leather.

34. The method of claim 29, wherein said substance is a flexible plastic.

35. The method of claim 29, wherein said substance is a textile.

36. The method of claim 29, wherein said at least one microorganism is a bacterium or fungus.

* * * * *